United States Patent [19]
Kong et al.

[11] Patent Number: 6,048,731
[45] Date of Patent: Apr. 11, 2000

[54] METHOD FOR CLONING AND PRODUCING THE SGRAI RESTRICTION ENDONUCLEASE

[75] Inventors: Huimin Kong, Wenham; Lauren S. Higgins, Bedford; Michael A. Dalton, Manchester, all of Mass.

[73] Assignee: New England Biolabs, Inc., Beverly, Mass.

[21] Appl. No.: 09/146,675

[22] Filed: Sep. 3, 1998

[51] Int. Cl.$^7$ ............................... C12N 9/22; C12N 15/55
[52] U.S. Cl. .................... 435/478; 435/199; 435/252.33; 435/320.1; 536/23.2
[58] Field of Search ................................ 435/320.1, 199, 435/252.33, 478; 536/23.2

[56] References Cited

U.S. PATENT DOCUMENTS

| | | | |
|---|---|---|---|
| 5,200,333 | 4/1993 | Wilson | 435/172.3 |
| 5,320,957 | 6/1994 | Brooks et al. | 435/172.3 |
| 5,492,823 | 2/1996 | Xu | 435/194 |

OTHER PUBLICATIONS

Roberts et al., Nucl. Acids Res. 26:338–350 (1998).
Kosykh et al., Mol. Gen. Genet. 178:717–718 (1980).
Mann et al., Gene 3:97–112 (1978).
Walder et al., Proc. Nat. Acad. Sci. 78:1503–1507 (1981).
Bougueleret et al., Nucl. Acids Res. 12:3659–3676 (1984).
Gingeras et al., Proc. Natl. Acad. Sci. USA 80:402–406 (1983).
Theriault et al., Gene 19:355–359 (1982).
Blumenthal et al., J. Bacteriol. 164:501–509 (1985).
Kiss et al., Nucl. Acids Res. 13:6403–6421 (1985).
Szomolanyi et al., Gene 10:219–225 (1980).
Janulaitis et al., Gene 20:197–204 (1982).
Kiss et al., Gene 21:111–119 (1983).
Walder et al., J. Biol. Chem. 258:1235–1241 (1983).
Piekarowicz et al., Nucl. Acids Res. 19:1831–1835 (1991).
Piekarowicz et al., J. Bacteriol. 173:150–155 (1991).
Fomenkov et al., Nucl. Acids Res. 22:2399–2403 (1994).
Lunnen et al., Gene 74(1):25–32 (1988).
Raleigh et al., Proc. Natl. Acad. Sci USA 83:9070–9074 (1986).
Heitman et al., J. Bacterol. 196:3243–3250 (1987).
Raleigh et al., Genetics 122:279–296 (1989).
Waite–Rees et al., J. Bacteriol. 173:5207–5219 (1991).
Ochman et al., Genetics 120:621–623 (1988).
Triglia et al., Nucl. Acids Res. 16:8186 (1988).
Silver et al., J. Cell. Biochem. (Supp) 13E:306, Abst. No WH239 (1989).
Ives et al., J. Bacteriol. 177:6313 (1995).
Matsudaira, P., J. Biol. Chem. 262:10035–10038 (1987).
Looney et al., Gene 80:193–208 (1989).
Nwankwo et al., Gene 64:1–8 (1988).
Kunkel et al., Methods of Enzym. 204:125–139 (1991).

*Primary Examiner*—Charles L. Patterson, Jr.
*Attorney, Agent, or Firm*—Gregory D. William

[57] ABSTRACT

The present invention relates to the recombinant DNA which encodes the SgrAI restriction endonuclease and the MspI modification methylase, and the production of SgrAI restriction endonuclease from the recombinant DNA.

6 Claims, 6 Drawing Sheets

FIG. 3A

```
         10                  30                  50
GTGCCCTTTACTTATAGCATTGAGGCAACAAGAAATCTGGCCACTACCGAGCGATGCATC
ValProPheThrTyrSerIleGluAlaThrArgAsnLeuAlaThrThrGluArgCysIle 70                  90                 110
CAAGATATTCGAAATGCGCCAGTGCGAAATCGTTCCACGCAGTTCCAGCTGGCTCAGCAA
GlnAspIleArgAsnAlaProValArgAsnArgSerThrGlnPheGlnLeuAlaGlnGln 130                 150                 170
AACATGCTCGCCTACACCTTCGGTGAGGTAATCCCTGGATTCGCTTCAGCTGGGATTAAC
AsnMetLeuAlaTyrThrPheGlyGluValIleProGlyPheAlaSerAlaGlyIleAsn 190                 210                 230
GGAATGaACTATCGGGACGTAATTGGGCGCCCCGTTGAAAATGCCGTGACAGAGGGAACT
GlyMetAsnTyrArgAspValIleGlyArgProValGluAsnAlaValThrGluGlyThr 250                 270                 290
CACTTTTTCCGAGACGATTTTCGCGTAGATTCAAATGCAAAGGCGAAGGTTGCCGGCGAT
HisPhePheArgAspAspPheArgValAspSerAsnAlaLysAlaLysValAlaGlyAsp 310                 330                 350
ATTTTCGAGATTGTGTCTTCTGCGGTCATGTGGAACTGCGCGGCTCGGTGGAACTCGCTG
IlePheGluIleValSerSerAlaValMetTrpAsnCysAlaAlaArgTrpAsnSerLeu 370                 390                 410
ATGGTGGgTGAAGGGTGGCGCTCTCAGCCGCGGTACAGTAgGCCGACGCTGAgTCCGTCT
MetValGlyGluGlyTrpArgSerGlnProArgTyrSerArgProThrLeuSerProSer 430                 450                 470
CCTCGCCGACAAGTGGCAGTTTTGAATTTGCCGCGCAGCTTTGACTGGGTCAGCCTTCTG
ProArgArgGlnValAlaValLeuAsnLeuProArgSerPheAspTrpValSerLeuLeu 490                 510                 530
GTCCCCGAATCGCAgGAAGTGATTGAgGAATTCAGGGCAGGCCTTCGGAAAGATGGCcTC
ValProGluSerGlnGluValIleGluGluPheArgAlaGlyLeuArgLysAspGlyLeu 550                 570                 590
GGGCTCCCcACTTCTACTCCCGATTTGGCAGTAGTTGTCCTCCCGGAAGAGTTCCAGAAT
GlyLeuProThrSerThrProAspLeuAlaValValValLeuProGluGluPheGlnAsn 610                 630                 650
GATGAAATGTGGCGGGAAGAAATAGCAGGGCTGACGCGCCCTAATCAAaTTCTTCTTTCG
AspGluMetTrpArgGluGluIleAlaGlyLeuThrArgProAsnGlnIleLeuLeuSer 670                 690                 710
GGAGCATATCAGCGGCTCCAAGGGCGGgTTCAGCCTGGAGAGATTTCCCTGGCTGTGGCC
GlyAlaTyrGlnArgLeuGlnGlyArgValGlnProGlyGluIleSerLeuAlaValAla 730                 750                 770
TTTAAGAgGAGCcTTCGAAGTGATCGGCTGTATCAGCCGCTCTACGAgGCGAACGTTATG
```

FIG. 3B

PheLysArgSerLeuArgSerAspArgLeuTyrGlnProLeuTyrGluAlaAsnValMet

```
          790                 810                 830
CAGTTGCTGCTTGAgGGTAAGCTTGGTGCGCCCAAgGTGGAATTCGAgGTTCATACGCTT
GlnLeuLeuLeuGluGlyLysLeuGlyAlaProLysValGluPheGluValHisThrLeu 850                 870                 890
GCTCCTGAgGGCACAAATGCCTTCGTTACGTATGAAGCGGCATCACTGTATGGGTTGGCG
AlaProGluGlyThrAsnAlaPheValThrTyrGluAlaAlaSerLeuTyrGlyLeuAla 910                 930                 950
GAAGGGAGGTCAGCCGTACATCGAGCAATCCGGGAGCTCTATGTTCCGCCGACCGCTGCC
GluGlyArgSerAlaValHisArgAlaIleArgGluLeuTyrValProProThrAlaAla 970                 990                1010
GATCTCGCACGCCGCTTCTTCGCGTTCTTGAACGAACGCATGGAGCTGGTGAACGGCTGA
AspLeuAlaArgArgPhePheAlaPheLeuAsnGluArgMetGluLeuValAsnGlyEnd
```

FIG. 4A

```
              10                  30                  50
TTGACCCGCTGTCAGTCCTCCCGGATAGCCTGTTGGCTTCCCACGAAAGGCTCACACTCC
LeuThrArgCysGlnSerSerArgIleAlaCysTrpLeuProThrLysGlySerHisSer 70                  90                 110
ATGACACCGCGCAAGGCCGTCTCTCTCTTCTCAGGCTGCGGAGGCTTTTGCGAGGGGGTA
MetThrProArgLysAlaValSerLeuPheSerGlyCysGlyGlyPheCysGluGlyVal 130                 150                 170
CGCCTCGCCGGTTTTTCAGTTGAGGCAGCCGTCGAGCTTGACCGATTCGCTGCAGTCACG
ArgLeuAlaGlyPheSerValGluAlaAlaValGluLeuAspArgPheAlaAlaValThr 190                 210                 230
TACCGCCACAACTTCCCCGAAGTTCCGCTTTTCGAGGGAGACGTTCATGACTTCCTCAAT
TyrArgHisAsnPheProGluValProLeuPheGluGlyAspValHisAspPheLeuAsn 250                 270                 290
GACTCGTCGGAGACGTGGCGTGGCGAAGCAGAGAGATTCTCCGACGTAAAAGCAGGGAAT
AspSerSerGluThrTrpArgGlyGluAlaGluArgPheSerAspValLysAlaGlyAsn 310                 330                 350
ATTGACCTGCTCTTCGGAGGGCCCCCATGCCAGGGCTACAGTCAGATTGGCACCAGAATC
IleAspLeuLeuPheGlyGlyProProCysGlnGlyTyrSerGlnIleGlyThrArgIle 370                 390                 410
CTGGACGATCCCCGTAATCAACTGTACGCGGAATATGTGCGGGTTCTTAAGACTCTCCGC
LeuAspAspProArgAsnGlnLeuTyrAlaGluTyrValArgValLeuLysThrLeuArg 430                 450                 470
CCTCGCGTTTTCTTGATGGAGAATGTCCCAAACATGCTCCTAATGGACAAGGGTCGGTTC
ProArgValPheLeuMetGluAsnValProAsnMetLeuLeuMetAspLysGlyArgPhe 490                 510                 530
AAGCGCGAGGTGTTGGCAGCTTTCGCAGAGGCCGGCTATTCGAATTGCGGCGTGACAGTT
LysArgGluValLeuAlaAlaPheAlaGluAlaGlyTyrSerAsnCysGlyValThrVal 550                 570                 590
GTTGCAGCCTCGGATCACGGAGTTCCCCAACTCCGGCGCAGAGCCATTTTCTTCGGCGTT
ValAlaAlaSerAspHisGlyValProGlnLeuArgArgArgAlaIlePhePheGlyVal 610                 630                 650
CGCGATGGGGAAAACCTAGGCGTTGACGCACATGCTTTTCTAGAAGCTGCTCTCGCGGCC
ArgAspGlyGluAsnLeuGlyValAspAlaHisAlaPheLeuGluAlaAlaLeuAlaAla 670                 690                 710
GAACGGAAGCCTGAAGTTTCTGTACGTCAGGCTATCGGCGATCTCCCGGAAGTGACTGCT
GluArgLysProGluValSerValArgGlnAlaIleGlyAspLeuProGluValThrAla 730                 750                 770
AGTCACTACGAGCCGGTGCGCTACCCTGTCACCCGCGCAAAAAAATCCGTTCCTCGACGAG
```

FIG. 4B

SerHisTyrGluProValArgTyrProValThrArgAlaLysAsnProPheLeuAspGlu

```
        790              810              830
ATGCGACTGAACCGCGATGGCCAGTGGTATTCACGCGCAGAGAAgTCCAAAAAATCCACT
MetArgLeuAsnArgAspGlyGlnTrpTyrSerArgAlaGluLysSerLysLysSerThr 850              870              890
GCCAAGGTTCTCCACAACCATCACACCAAAGAGATTCAAGCCCGCCGGAAAGCCCTTATC
AlaLysValLeuHisAsnHisHisThrLysGluIleGlnAlaArgArgLysAlaLeuIle 910              930              950
GCACTCCTGGCTCCAGGCGCTAAAGCAGATTCCCTACCGAAAGAAATCTGGAATGGTGCG
AlaLeuLeuAlaProGlyAlaLysAlaAspSerLeuProLysGluIleTrpAsnGlyAla 970              990              1010
CGCCTTGAGAAGTGGCGACGACTGCACCCAGACAAGCCGGCATACACGATTTTGGCGCAG
ArgLeuGluLysTrpArgArgLeuHisProAspLysProAlaTyrThrIleLeuAlaGln 1030             1050             1070
ATGCATCGCGACATGTCTGAATGGGTGCATCCTGACTATGAGCGATGGATCACTGTTCGC
MetHisArgAspMetSerGluTrpValHisProAspTyrGluArgTrpIleThrValArg 1090             1110             1130
GAGGCAGCGCGCCTCCAGTCTTTTCCATGATGGATTCGTATTCCAGACCAGCGAATGGCAG
GluAlaAlaArgLeuGlnSerPheHisAspGlyPheValPheGlnThrSerGluTrpGln 1150             1170             1190
ATGTTGAAGCAGATCGGAAACGCCGTTCCTCCGCTGATGGCACGGGCTTTGGCAGCTGTT
MetLeuLysGlnIleGlyAsnAlaValProProLeuMetAlaArgAlaLeuAlaAlaVal 1210             1230             1250
GCGAGCCGTTCACTGGACGTGATGGAAGATTCATCTACGGACACGCGGTTTAGCGTCCCG
AlaSerArgSerLeuAspValMetGluAspSerSerThrAspThrArgPheSerValPro 1270             1290
ATTCAGCAGACGTTGGAACTAGTGCCCTGA
IleGlnGlnThrLeuGluLeuValProEnd
```

FIG. 5

```
            10                        30                        50
GTGCCTGACCTGTGCTCTCACCTTGGCTTGGCTGTACGTGCTGTGAGGCTGCGACGCGGC
ValProAspLeuCysSerHisLeuGlyLeuAlaValArgAlaValArgLeuArgArgGly 70                        90                       110
TGGTCTCAGGAGCTGTTGTCGGAAAAATCTGGATTGGATCGCACATATGTGAGTGGCCTT
TrpSerGlnGluLeuLeuSerGluLysSerGlyLeuAspArgThrTyrValSerGlyLeu 130                       150                       170
GAGCGCGGGCGGCGGAACCCTGCGCTACTCACCTTGGCCCGTTTGGCTGATGCGCTTGAA
GluArgGlyArgArgAsnProAlaLeuLeuThrLeuAlaArgLeuAlaAspAlaLeuGlu 190                       210                       230
GTTCCGTTGTCTGAGCTAATCCGTGATGCCGAGGAGAATTCAGGTGCCCTTTACTTATAG
ValProLeuSerGluLeuIleArgAspAlaGluGluAsnSerGlyAlaLeuTyrLeuEnd
```

METHOD FOR CLONING AND PRODUCING THE SGRAI RESTRICTION ENDONUCLEASE

BACKGROUND OF THE INVENTION

The present invention relates to the recombinant DNA which encodes the SgrAI restriction endonuclease and modification methylase, and the production of SgrAI restriction endonuclease from the recombinant DNA. SgrAI restriction endonuclease is originally isolated from *Streptomyces griseus*. It recognizes the DNA sequence 5' CRCCGGYG 3' and cleaves the phosphodiester bond 5' to the second C of the recognition sequence to produce a 4 base 5' extension.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Type II restriction endonucleases act by recognizing and binding to particular sequences of nucleotides (the 'recognition sequence') along the DNA molecule. Once bound, they cleave the DNA molecule at specific positions. Different restriction endonucleases have affinity for different recognition sequences. About 2900 restriction endonucleases have been characterized so far, and they recognize 212 different recognition sequences (Roberts, et al. *Nucleic Acids Res.* 26: 338–350 (1998)).

It is thought that in nature, restriction endonucleases play a protective role in the welfare of the bacterial cell. They enable bacteria to resist infection by foreign DNA molecules like bacteriophages and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify the target nucleotide within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiable foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719, (1980); HhaII: Mann et al., *Gene* 3:97–112, (1978); PstI: Walder et al., *Proc. Nat. Acad. Sci.* 78:1503–1507, (1981))). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach which is being used to clone a growing number of systems, involves selection for an active methylase gene (refer to U.S. Pat. No. 5,200,333 and BsuRI: Kiss et al., *Nucl. Acid. Res.* 13:6403–6421, (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al, *Gene* 20:197–204 (1982); BsuRI: Kiss and Baldauf, *Gene* 21:111–119, (1983); and MspI: Walder et al., *J. Biol. Chem.* 258:1235–1241, (1983)).

Another method for cloning methylase and endonuclease genes is based on a colorimetric assay for DNA damage (see, U.S. Pat. No. 5,492,823). When screening for a methylase, the plasmid library is transformed into the host *E. coli* strain such as AP1-200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et. al., *Nucl. Acids Res.* 19:1831–1835, (1991) and Piekarowicz, et. al. *J. Bacteriology* 173:150–155 (1991)). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et. al. *Nucl. Acids Res.* 22:2399–2403 (1994)).

Sometimes the straight-forward methylase selection method fails to yield a methylase (and/or endonuclease) clone due to various obstacles. See, e.g., Lunnen, et al., *Gene,* 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see, U.S. Pat. No. 5,320, 957).

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074 (1986)) or methylated adenine (Heitman and Model, *J. Bact.* 196:3243–3250 (1987); Raleigh,et al., *Genetics*, 122:279–296, (1989) Waite-Rees, et al., *J. Bacteriology*, 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA– and McrB– or Mrr–) in which these systems are defective.

A third potential difficulty is that some restriction endonuclease and methylase genes may not express in *E. coli* due to differences in the transcription machinery of the source organism and *E. coli*, such as differences in promoter and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

A unique combination of methods was used to directly clone the SgrAI endonuclease gene and express the gene in an *E. coli* strain premodified by MspI methylase. To clone the SgrAI endonuclease gene directly, both the N-terminal amino acid sequence and a stretch of internal amino acid sequence of highly purified native SgrAI restriction endonuclease were determined. Degenerate primers were designed based on the amino acid sequences and PCR techniques were used to amplify the DNA fragment that encodes the SgrAI endonuclease protein. The PCR product was sequenced and the information was used to design primers for inverse PCR reactions. By chromosome walking via inverse PCR, the endonuclease open reading frame, sgrAIR, was deduced. Continuing with inverse PCR, two open reading frames were found upstream of the endonuclease gene. Blast analysis suggested that the genes encoded a C5 methylase (sgrAIM) and a C protein (control protein, sgrAIC).

SgrAI methylase was not fully modifying host DNA and therefore could not be used to protect host DNA against SgrAI endonuclease digestion. MspI methylase recognizes 5' CCGG 3', which is the center part of the SgrAI sequence 5' CRCCGGYG 3'. MspI methylase is able to protect DNA against SgrAI endonuclease digestion. SgrAI endonuclease gene was cloned into T7 expression vector pET21at and transformed into an *E. coli* strain which was premodified by MspI methylase. This recombinant *E. coli* strain (NEB#1158) produces about 120,000 units SgrAI endonuclease per gram cell. The yield of recombinant SgrAI endonuclease is 100-fold higher than the yield of native endonuclease from *Streptomyces griseus* (1200 units/gram).

BRIEF DESCRIPTION OF THE DRAWINGS

FIG. 3 shows the DNA sequence of sgrAIR gene and its encoded amino acid sequence (SEQ ID NO:1).

FIG. 4 shows the DNA sequence of sgrAIM gene and its encoded amino acid sequence (SEQ ID NO:2).

FIG. 5 shows the DNA sequence of sgrAIC gene and its encoded amino acid sequence (SEQ ID NO:3).

DETAILED DESCRIPTION OF THE INVENTION

The cloning of the SgrAI restriction endonuclease gene from *Streptomyces griseus* proved to be challenging. A methylase selection strategy was tried but no methylase expressing clones were isolated. A direct cloning method was then used to clone the endonuclease gene and a cross-protective MspI methylase was used to express the SgrAI endonuclease gene. The method described herein by which the SgrAI restriction endonuclease is preferably cloned and expressed in the *E. coli* utilizes the following steps:

1. Purify the SgrAI restriction endonuclease to near homogeneity and determine its N-terminal as well as a stretch of internal amino acid sequences.

A unique combination of ion-exchange chromatography columns were use to purify native SgrAI restriction endonuclease to near homogeneity. Four column chromatographies were used to purify SgrAI endonuclease protein. They were heparin-hyper D column, Source™-15Q column, Source™-15S FPLC column, and Heparin TSK column. The purification yielded a single protein band at approximately 38 kDa on an SDS-PAGE The N-terminal 29 amino acid residues were determined by sequential degradation of the purified protein on an automated sequencer. To determine its internal protein sequence, a 14-kDa polypeptide fragment was obtained following cyanogen bromide digestion of the 38-kDa SgrAI protein. The sequence of 9 amino acid residues of this 14-kDa was determined. This 9-amino acid sequence differs from the sequence of the N-terminal 29 amino acid residues, suggesting it was derived from internal SgrAI protein fragment.

2. Amplification of 5' region of SgrAI endonuclease gene and subsequent cloning into plasmid.

Degenerate primers were designed based on the N-terminal and internal amino acid sequences and these primers were used to PCR amplify the 5' end of the endonuclease gene. PCR products were cloned into plasmid pCAB16 and sequenced. The 375-bp PCR fragment which corresponds to the SgrAI endonuclease gene was then identified by comparing the amino acid sequences deduced from the cloned DNA with the N-terminal and internal amino acid sequences of the SgrAI endonuclease protein.

3. Chromosome walking via inverse PCR to isolate the SgrAI endonuclease and methylase genes.

Figure 1:
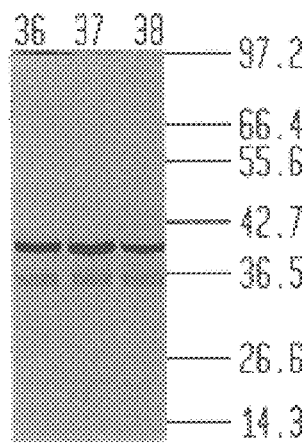
FIG. 1 shows the purified native SgrAI endonuclease on a SDS-PAGE.
Figure 2:
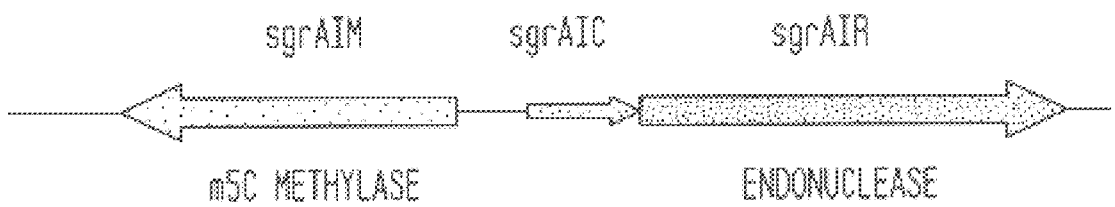
FIG. 2 shows the gene organization of SgrAI restriction-modification system. sgrAIR: SgrAI endonuclease gene; sgrAIM: SgrAI methylase gene; sgrAIC: contral gene.

To clone the entire SgrAI endonuclease gene as well as its corresponding DNA methylase gene, inverse PCR techniques were adopted to amplify DNA adjacent to the original 375-bp endonuclease gene fragment (Ochman, et al., *Genetics*, 120:621 (1988), Triglia, et al., *Nucl. Acids Res.*, 16:8186 (1988) and Silver and Keerikatte, *J. Cell. Biochem.*, (Suppl.) 13E:306, Abstract No. WH239 (1989)) and the amplified products were sequenced. In total, three rounds of inverse PCR were performed. At that point, three open reading frames (ORF) had been identified (FIG. 2). The 1020-bp endonuclease gene (sgrAIR) encodes a 339-amino acid protein with a deduced molecular weight of 37999, which agrees with the observed molecular mass of SgrAI endonuclease (FIG. 1). A 240-bp small ORF, sgrAIC, is found upstream of the sgrAIR. It exhibits extensive sequence homology to the control (C) genes found in several other restriction-modification systems (Ives et al., *J. Bacteriology*, 177:6313 (1995)). Adjacent to the 5' end of the control gene is a 1290-bp methylase gene sgrAIM. The protein sequence deduced from sgrAIM gene shares significant similarity with other m$^5$C cytosine methylases.

4. Expression of SgrAI endonuclease gene using cross-protection of MspI methylase.

Because SgrAI methylase could not provide enough modification to the host DNA (probably due to its poor expression in *E. coli*), MspI methylase was used to stabilize bacterial hosts containing the SgrAI endonuclease. The SgrAI endonuclease gene was cloned into pET21a plasmid downstream of a T7 promoter and transformed into an *E. coli* strain carrying the MspI methylase gene on a separate pACYA184 vector compatible with the expression vector pET21a. Vectors containing inserts of the desired size were identified by miniprep procedures. These clones were grown to mid-log phase and induced with IPTG. The cells were then harvested by centrifugation, resuspended in sonication buffer and lysed by sonication. The extracts were assayed for SgrAI endonuclease activity.

The following Example is given to illustrate embodiments of the present invention as it is presently preferred to practice. It will be understood that this Example is illustrative, and that the invention is not to be considered as restricted thereto except as indicated in the appended claims.

The references cited above and below are hereby incorporated by reference herein.

EXAMPLE 1

Purification of the SgrAI Endonuclease and Determining its Protein Sequence

1. Purification of the SgrAI restriction endonuclease from *Streptomyces griseus* to near homogeneity:

*Streptomyces griseus* cells were propagated at 30° C. The cells were harvested by centrifugation after 20 hours growth and stored at −70° C. until used. All of the following procedures were performed on ice or at 4° C. 1184 g of cell pellet (wet weight) was resuspended in 1855 ml of sonication buffer (20 mM Tris-HCl, 1 mM Dithiothreitol (DTT), 0.1 mM EDTA, 0.1 M NaCl, pH 7.5) and broken with a Manton-Gaulin homogenizer. The extract was centrifuged at 14,000 rpm for 10 minutes at 4° C.

The supernatant was loaded onto a 500 ml heparin-hyper D column (BioSepra, Marlborough, Mass.) equilibrated with buffer A.1 (50 mM NaCl, 20 mM KPO4, PH 7.0, 0.1 mM EDTA, 10 mM β-mercaptoethanol and 5% glycerol). The column was washed with 800 ml of buffer A.1, followed by a 4 L linear gradient from 50 mM NaCl to 900 mM NaCl in buffer A (20 mM KPO4, PH 7.0, 0.1 mM EDTA, 10 mM β-mercaptoethanol and 5% glycerol). 25 ml fractions were collected. Fractions were assayed for SgrAI restriction activity with lambda DNA and the peak of restriction enzyme activity was found to elute from the column between 0.53 to 0.60 M NaCl and was pooled. The amount of SgrAI endonuclease was estimated to be 600,000 units.

This heparin-hyper D pool was dialyzed against 8 L of 100 mM NaCl in buffer B (20 mM Tris, pH 8.0, 0.1 mM EDTA, 10 mM β-mercaptoethanol and 5% glycerol, final pH of 7.8). The dialyzed pool was diluted with buffer B to a final concentration of 50 mM NaCl and applied to a 90 ml Source™-15Q column (Pharmacia Biotech, Piscataway, N.J.) equilibrated in buffer B.1 (50 mM NaCl, 20 mM Tris, pH8.0, 0.1 mM EDTA, 10 mM β-mercaptoethanol and 5% glycerol, final pH of 7.8). The column was washed with 200 ml of buffer B1 followed by a 1 L linear gradient of 50 mM NaCl to 700 mM NaCl in buffer B. 10 ml fractions were collected. Fractions were assayed for SgrAI activity with lambda DNA. The peak of restriction enzyme activity eluted between 200 and 232 mM NaCl and 6 fractions were pooled.

This Source-15Q pool contained approximately 240,000 units of SgrAI activity. Approximately, 120,000 units flowed through the Source-Q and perhaps the enzyme is dying and therefore reducing the total number of units. The 6 pooled fractions were diluted with 3.5 volumes of buffer A and loaded onto a 8 ml HR 10/10 Source™-15S FPLC column (Pharmacia: Piscataway, N.J.) equilibrated with Buffer A.1. The column was washed with 16 ml of buffer A.1 and then a 100 ml linear gradient from 50 mM NaCl to 700 mM NaCl in Buffer A was performed. 2.5 ml fractions were collected. Fractions were assayed for SgrAI activity with lambda DNA. Approximately 78,000 units of activity flowed through the column and 10,000 units were eluted in the first 12 fractions.

The 12 fractions were combined and diluted to 50 mM NaCl in buffer B. The diluted pool was then loaded onto a 10 ml HR 10/10 Heparin 5PW TSK Guardgel column (Toso Haas; Philadelphia, Pa.) equilibrated with buffer B1. The column was washed with 20 ml buffer B1 followed by a 100 ml linear gradient from 50 mM NaCl to 100 mM NaCl in buffer B. 1.5 ml fractions were collected. Fractions were assayed for SgrAI activity with λDNA. The peak of the enzyme activity eluted at 0.56 M NaCl. Approximately 10,000 units of SgrAI activity were purified to near homogeneity. 20 UL of the peak fractions (36, 37 and 38) were loaded onto an SDS-PAGE protein gel and subjected to electrophoresis. The gel was stained with Coomassie blue R-250 and a prominent band at approximately 38 kDa corresponding to the SgrAI restriction endonuclease activity was observed (FIG. 1).

2. Determining the N-terminal and internal protein sequences of SgrAI endonuclease The SgrAI restriction endonuclease, prepared as described was subjected to electrophoresis and electroblotted according to the procedure of Matsudaira (Matsudaira, P., *J. Biol. Chem.* 262:10035–10038, 1987), with modifications as previously described (Looney, et al., *Gene* 80:193–208, (1989). The membrane was stained with Coomassie blue R-250 and the protein band of approximately 38 kDa was excised and subjected to sequential degradation on an Applied BioSystems Division, Perkin-Elmer Corporation (Foster City, Calif.) Model 407A gas phase protein sequencer (Waite-Rees, et al. *J. Bacteriol.* 173:5207–5219 (1991). The first 27 residues of the 38 kDa protein corresponded to (M)-F-T-Y-S-I-E-A-T-(?)-N-L-A-T-T-E-H(?)-(?)-I-Q-D-I-R(?)-N-A-P-V (SEQ ID NO:4).

A 14-kDa polypeptide fragment was purified after digesting the 38-kDa R.SgrAI with Cyanogen Bromide. The N-terminal protein sequence of this 14 kDa was determined as: M-V-G-E-G-W(?)-H(?)-S-Q-P-G(?)-Y(?) (SEQ ID NO:5).

EXAMPLE 2

Cloning of the SgrAI Restriction-Modification Genes

1. Purification of genomic DNA from *Streptomyces griseus*

To prepare the genomic DNA of *Streptomyces griseus*, 5 g of cells were resuspended in 10 ml of 25% Sucrose, 50 mM Tris, pH 8.0 and mixed until the solution was homogenous. Five ml of 0.25 M EDTA, pH 8.0 plus 3 ml of freshly-prepared 10 mg/ml lysozyme in 0.25M Tris-HCl (pH 8.0) was added and the solution was incubated on ice for 2 hours. 12 ml of Lytic mix (1% Triton-X100, 50 mM Tris, 62 mM EDTA, pH 8.0) and 2.5 ml of 10% SDS were then added and the solution was gently mixed. The solution was extracted with one volume of equilibrated phenol/chloroform (50:50, v/v) and the aqueous phase was recovered. The aqueous solution was then dialyzed against four changes of 2 L of 10 mM Tris-HCl (pH 8.0), 1 mM EDTA. The dialyzed solution was digested with RNase (100 μg/ml) at 37° C. for 1 hour. The DNA was precipitated by the addition of 1/10th volume 5 M NaCl and 0.55 volume of 2-propanol and spooled on a glass rod. The DNA was air dried and dissolved in 15 ml TE (10 mM Tris, 1 mM EDTA, pH 8.0) to a concentration of approximately 160 μg/ml and stored at 4° C.

2. Cloning the 5' region of the SgrAI endonuclease gene into pCAB16 pCAB16 was digested with BsaAI by incubating the vector for 1 hour at 37° C. in the conditions described below.

120 μl pCAB 16 (6–12 μg)
10 μl BsaAI (50U)
40 μl 10× NEB Buffer #3
230 μl dH$_2$O The BsaAI in the reaction was heat killed by incubating for 15 minutes at 75° C. The vector was then dephosphorylated by incubating 100 μl (2 μg) of digested vector with 1 unit of shrimp alkaline phosphatase in 100 mM MgCl$_2$ for 1 hour at 37° C.

Degenerate primers were designed based on the following N-terminal and internal amino acid sequences: 1) F-T-Y-S-I-E (N-terminal) (SEQ ID NO:6) and 2) M-V-G-E-G-W (internal) (SEQ ID NO:7). They were designed to hybridize with the 5' end of the SgrAI endonuclease gene and with an internal segment of the gene respectively. The primers are oriented in opposite directions relative to each other.

Primer N-term. 5' TT(TC)AC(N)TA(TC)AG(TC)AT(TCA)GA 3' (SEQ ID NO:8)

Primer internal 5' CCA(N)CC(TC)TC(N)CC(N)ACCAT 3' (SEQ ID NO:9)

These primers were synthesized and each was kinased by incubating 1 μg of primer with 10 units of T4 Polynucleotide Kinase, 2 μl 10× T4 Polynucleotide Kinase, and 1 μl of 10 mM ATP, in a 20 μl reaction volume at 37° C. for 30 minutes. The kinase was heat inactivated by incubating the reaction at 65° C. for 10 min.

In the reaction that was successful in amplifying the product, a reaction mix was made by combining:

10 μl of 10× Vent Thermo Pol Buffer
10 μl of 2 mM dNTP solution
1.5 μl of kinased primer N-term (75 ng)
1.5 μl of kinased primer internal (75 ng)
0.6 μl of 100 mM MgSO$_4$ (4 mM Mg$^{++}$ final concentration)
0.46 μl of purified bacterial DNA template (~100 ng)
74 μl dH$_2$O
2 μl (4 units) of Vent Exo-polymerase NEB#257

The PCR amplification conditions were: 32 cycles of 95° C. for 30 seconds, 50° C. for 1 minute and 72° C. for 45 seconds. 100 μl of the PCR reaction was electrophoresed on a 3% low melt, NuSieve, Tris-Acetate agarose gel. The approximately 375-bp DNA band was cut out and the gel slice was incubated at 65° C. for 10 minutes. The temperature was reduced to 40° C. and an in-gel ligation was performed by combining the following at 40° C.:

2.7 μl prepared pCAB16 (50 ng)
10 μl PCR product (40 ng)
5 μl 10× T4 DNA Ligase Buffer
1 μl T4 DNA Ligase (400 units)
1 μl Beta-Agarase (1 unit)
30.3 μl dH$_2$O The reaction was incubated at 37° C. for one hour and then at 16° C. overnight. 10 μl of the overnight ligation reaction was transformed into 50 μl 50× competent ER2502 cells by combining the DNA and cells and incubating on ice for 20 minutes followed by 2 minutes at 37° C. The entire volume was plated on an Ampicillin plate and incubated overnight at 37° C. Colonies that grew were inspected for the correct plasmid construct by purifying the plasmid DNA (Quiagen QIAprep Spin Miniprep Kit) and digesting with BsiHKAI to see if the PCR product was cloned into the vector.

7 μl miniprep
2 μl 1 mg/ml BSA
2 μl 10× NEB #3
1 μl BsiHKAI
8 μl dH$_2$O

The above reaction was incubated at 65° C. for 1 hour. Minipreps containing the correct size insert were DNA sequenced. The DNA sequence was translated in six frames to check that the amino acid sequence translation corresponded with the N-terminal and internal amino acid sequence that the degenerate primer sequences were based on.

3. Chromosome walking via inverse PCR to isolate the SgrAI endonuclease and methylase genes A) Prepare genomic DNA—Two templates were prepared for the first inverse PCR reactions; Sau3AI and AvaII. In the case of Sau3AI, 1.5 μg of bacterial DNA was digested with 20 units of Sau3AI restriction endonuclease in 1× supplemented with BSA to a final concentration of 0.1 mg/ml in a 50 μl reaction volume. In the case of AvaII, 1.5 μg of bacterial DNA was digested with 50 units of AvaII restriction endonuclease in 1× NEBuffer #4 in a 50 μl reaction volume. Both reactions were incubated at 37° C. for one hour, phenol/chloroform extracted, ethanol precipitated, resuspended in 40 μl of dH$_2$O and the final concentrations were deduced by running 13 μl on a 1% agarose gel. The digests were then circularized by incubating the remaining 37 μl (~1 μg) in 1× T4 DNA Ligase Buffer with 3000 units of T4 DNA Ligase in a 500 μl reaction volume at 16° C. overnight. A portion of this circularization ligation reaction was then used as the template for subsequent inverse PCR reactions.

B) Sau3AI and AvaII inverse PCR reactions—A set of inverse PCR primers were synthesized based on the DNA sequence of the piece of the SgrAI endonuclease gene cloned into pCAB16:

```
5' GAC TAT CGG GAC GTA ATT GG 3'   (SEQ ID NO:10)
   (180-181)

5' CAT TCC GTT AAT CCC AGC TG 3'   (SEQ ID NO:11)
   (180-182)
```

Inverse PCR was carried out using primers 180–181 and 180–182 and the above mentioned DNA templates. An 890-bp product was observed in the Sau3AI circular template PCR reaction, and a 2 kb product was observed in the AvaII circular template PCR reaction. These two products were gel purified and resuspended in 40 μl dH₂O. These PCR products were then sequenced using an ABI 373 automated sequencing system according to the manufacturer's instructions, using the PCR primers above as the sequencing primers. The AvaII 2-kb inverse PCR product contained new DNA sequence almost exclusively upstream of the sgrAIR gene and the 2 kb made up the entire coding regions of both a control protein and a C5 methylase (FIG. 2). The DNA sequence of the Sau3AI PCR product expanded the DNA sequence of sgrAIR gene by revealing 360 new base-pairs.

C. BsaHI inverse PCR reactions—Two inverse PCR primers complementary to newly read sequence from the Sau3AI PCR product were then synthesized, as below, and used in an inverse PCR reaction. Template preparation, inverse PCR, purification and DNA sequencing were performed as above but BsaHI was used to create the template as opposed to Sau3AI or AvaII. A 900-bp PCR product was generated and sequenced. The sequence revealed the complete open reading frame of sgrAIR gene.

```
5' TCG GGC TCC CCA CTT CT 3'       (SEQ ID NO:12)
   (181-61)

5' GGC CAT CTT TCC GAA GGC CTG 3'  (SEQ ID NO:13)
   (181-62)
```

EXAMPLE 3

Expression of the SgrAI Restriction Endonuclease

1. Cloning the MspI methylase on a compatible vector

An approximately 3028-fragment was air HindIII/EcoRI fragment was excised from pNW106RM2-3 (D. O. Nwankwo et al. *Gene* 64:1–8 (1988)) and ligated into Bluescript SK-cut with the same enzymes. The resultant construct was named pBAD. This plasmid was mutagenized as described by Kunkel (T. A. Kunkel,et al., *Methods of Enzymology* 204:125–139 (1991)) using the oligonucleotide 5' CAATCTTTCTGGATCCTACTTG 3' (SEQ ID NO:14). This created a BamHI restriction site between the divergently transcribed MspI endonuclease and methylase genes. One such mutagenized construct was identified and named pBAF1. The approximately 1462 base pair BamHI/BglII restriction fragment from pBAF1 that contained the MspI methylase gene (mspIM) was cloned into pACM8 cut with BamHI. pACM8 is a derivative of pACYC184 that encodes kanamycin and chloramphenicol resistant genes, and contains regions of the lac operon. The insertion site in pACM8 is upstream of the lac sequences, and the constructs were screened for an mspIM insert that was transcribed in the same orientation as the lac sequences. One such construct was named pBAK1. The plasmid pBAK1 containing the mspIM gene was found to be completely protected against MspI endonuclease as well as SgrAI endonuclease digestions.

2. Cloning and expression of the SgrAI endonuclease gene

The SgrAI endonuclease gene (sgrAIR) was expressed by inserting the gene into a expression vector, pET21a, directly downstream of a strong inducible T7 promoter and a conserved ribosome binding site (RBS). To accomplish this, two oligonucleotide primers were made utilizing the DNA sequence data. The forward oligonucleotide primer contained a BamHI site to facilitate cloning, a stop codon in frame with the lacZ gene to terminate translation of the lacZ protein, RBS, seven nucleotide spacer between the RBS and the ATG start codon of the SgrAI endonuclease gene and 20 nucleotides complementary to Streptomyces griseus DNA for hybridization:

```
5'- CGCGGATCCTAAGGAGGTGATCAGGTGCCCTTTACTTATAGCAT -3'   (SEQ ID NO:15)
    (184-19)
```

The reverse primer was designed to hybridize to *Streptomyces griseus* DNA at the 3' end of the sgrAIR gene. It contained a XhoI restriction site to facilitate cloning.

```
                                                      (SEQ ID NO:16)
5'- AACCCTCGAGCCTTTCAGCCGTTCACCAGC -3'
    (184-20)
```

These two primers were used to amplify the sgrAIR gene from *Streptomyces griseus* genomic DNA by combining:

10 μl 10× Vent ThermoPol Buffer
10 μl of 2 mM dNTPs
0.75 μl (150 ng) Streptomyces griseus genomic DNA
1 μl primer 184-19 (75 ng)
5 μl primer 184-20 (75 ng)
75.25 μl dH₂O
1 μl (0.1 units) Deep Vent™ polymerase
1 μl Taq DNA polymerase (5 units)

and amplifying for 25 cycles at 95° C. for 30 seconds, 58° C. for 1 minute and 72° C. for 1.5 minutes. The amplification product of approximately 1000 bp was purified using the Promega Wizard PCR Preps Kit. 2 μg of pET21at vector and the remaining PCR product (~2 μg) were both digested with 50 units of BamHI and 20 units of XhoI, supplemented with 0.1 mg/ml BSA in 1× NEB BamHI buffer in a 50 μl reaction that was incubated at 37° C. for one hour. The digests were run on a 1% low melting-point NuSieve agarose gel in TAE buffer. The DNA bands were cut out of the gel, and treated with beta-agarase and ethanol precipitated. The DNAs were resuspended in 20 μl TE and 75 ng of the PCR product was ligated into 100 ng pET21at vector in 1× NEB T4 DNA Ligase Buffer supplemented with 400 units of T4 DNA Ligase. The reaction was incubated at 37° C. for one hour. 7 μl of the ligation reaction was transformed into *E. coli* strain ER2502 previously modified with the MspI methylase gene construct pBAK1. Out of six individual transformants analyzed, three contained sgrAIR gene. Two of the three expressed SgrAI endonuclease activity. One of these plasmid constructs, the pETsgrAIRI, was selected for producing the SgrAI endonuclease. The *E. coli* strain which contains both pETsgrAIRI and pBAK1 plasmids was designated as NEB #1158. The yield of recombinant SgrAI in strain NEB #1158 was approximately 120,000 units/gram of cells.

3. Producing the recombinant SgrAI restriction endonuclease from *E. coli* NEB #1158

*E. coli* NEB #1158 was grown to mid-log phase in a fermenter containing Luria-Bertani (LB) medium with ampicillin (100 µg/ml) and kanamycin (50 µg/ml). The culture was induced by the addition of IPTG to a final concentration of 0.3 mM and allowed to continue growing for 16 hours. The cells were harvested by centrifugation and may be stored at −70° C. or used immediately.

Purification of the SgrAI restriction endonuclease from NEB #1158 can be accomplished by a combination of standard protein purification techniques, such as affinity-chromatography or ion-exchange chromatography, as outlined in Example 1 above. The SgrAI restriction endonuclease obtained from this purification is substantially pure and free of non-specific endonuclease and exonuclease contamination.

A sample of the *E. coli* NEB#1158 which contains both pETsgrAIRI and pBAK1 plasmids has been deposited under the terms and conditions of the Budapest Treaty with the American Type Culture Collection on Sep. 3, 1998 and received ATCC Accession Number 98865.

What is claimed is:

1. Isolated DNA coding for the SgrAI restriction endonuclease, wherein the isolated DNA is obtainable from *Streptomyces griseus*.

2. A recombinant DNA vector comprising a vector into which a DNA segment coding for the SgrAI restriction endonuclease has been inserted.

3. A cloning vector which comprises the isolated DNA of claim 1.

4. A host cell transformed by the vector of claims 2 or 3.

5. A method of producing a SgrAI restriction endonuclease comprising culturing a host cell transformed with the vector of claim 2 or 3 under conditions suitable for expression of said endonuclease.

6. A novel method of cloning and expressing SgrAI endonuclease gene comprising using cross-protective MspI methylase.

* * * * *

UNITED STATES PATENT AND TRADEMARK OFFICE
CERTIFICATE OF CORRECTION

PATENT NO. : 6,048,731
DATED : April 11, 2000
INVENTOR(S) : Huimin Kong, Lauren S. Higgins and Michael A. Dalton It is certified that error appears in the above-identified patent and that said Letters Patent is hereby corrected as shown below:

Column 2,
Line 5, replace "Genet" with --Genet.--
Line 5, replace "719" with --718--
Line 7, replace "(1981)))" with -- (1981)) --
Line 18, replace "Acid." with --Acids--
Line 22, after "509" delete --,--
Line 26, replace "Acid." with --Acids--
Line 26, after "6421" delete --.--
Line 31, after "225" delete --.--
Line 32, replace "et al," with --et al.,--
Line 33, after "119" delete --,--
Line 34, after "1241" delete --,--
Line 36, after "see" delete --,--
Line 48, replace "Piekarowicz, et." with --Piekarowicz, et--
Line 49, after "1835" delete --,--
Line 49, replace "Piecarowicz, et. al." with --Piecarowicz et al.,--
Line 58, replace "Xu et. al." with --Fomenkov et al.,--
Line 62, after "Lunnen," delete --,--
Line 63, after "Gene" delete --,--

Column 3,
Line 12, after "Raleigh" delete --,--
Line 13 after "Genetics" delete --,--
Line 13, after "296" delete --,--
Line 13 after "Waite-Rees" delete --,--
Line 14, after "Bacteriology" delete --,--

UNITED STATES PATENT AND TRADEMARK OFFICE
CERTIFICATE OF CORRECTION

PATENT NO. : 6,048,731
DATED : April 11, 2000
INVENTOR(S) : Huimin Kong, Lauren S. Higgins and Michael A. Dalton It is certified that error appears in the above-identified patent and that said Letters Patent is hereby corrected as shown below:

Column 4,
Line 8, replace "FIG. 3 shows" with --FIGS. 3A and 3B show--
Line 10, replace "FIG. 4 shows" with --FIGS. 4A and 4B show--
Line 31, replace "use" with --used--
Line 37, after "SDS-PAGE" insert --.--
Line 64, after "Ochman" delete --,--
Line 65, after Genetics" delete --,--
Line 65, after "621" insert ---623--
Line 65, after "Triglia" delete--,--
Line 65, after "Res." delete --,--
Line 66, after "Keerikatte" delete--,--
Line 66, after "Biochem." delete --,--

Column 5,
Line 11, after "Bacteriology" delete --,--

Column 6,
Line 20, replace "a" with --an--
Line 50, after "descibed" insert --,--
Line 52, after "10038" delete --,--
Line 52, replace "1987)" with --(1987))--
Line 54, after "208" delete --,--
Line 54, after "(1989)" insert --)--
Line 59, after "Waite-Rees" delete --,--
Line 59, after "et al." insert --,--
Line 60, after "(1991)" insert --)--

Column 9,
Line 54, after "et al." insert --,--
Line 57, after "Kunkel" delete --,--

UNITED STATES PATENT AND TRADEMARK OFFICE
CERTIFICATE OF CORRECTION

PATENT NO. : 6,048,731
DATED : April 11, 2000
INVENTOR(S) : Huimin Kong, Lauren S. Higgins and Michael A. Dalton It is certified that error appears in the above-identified patent and that said Letters Patent is hereby corrected as shown below:

Column 10,
Line 11, replace "a" with --an--
Line 18, replace "spacer" with --spacers--
Line 20, replace "Streptomyces griseus" with --*Streptomyces griseus*--
Line 37, replace "ıı1" with --µ1--
Line 40, replace "Streptomyces griseus" with --*Streptomyces griseus*--

Claim 5,
Line 1, replace "a" with --an--.

Signed and Sealed this

Twenty-sixth Day of June, 2001

*Attest:*

NICHOLAS P. GODICI
*Attesting Officer*     *Acting Director of the United States Patent and Trademark Office*

SEQUENCE LISTING

<160> NUMBER OF SEQ ID NOS: 16

<210> SEQ ID NO 1
<211> LENGTH: 1020
<212> TYPE: DNA
<213> ORGANISM: Streptomyces griseus
<220> FEATURE:
<221> NAME/KEY: CDS
<222> LOCATION: (1)..(1017)

<400> SEQUENCE: 1

```
gtg ccc ttt act tat agc att gag gca aca aga aat ctg gcc act acc        48
Val Pro Phe Thr Tyr Ser Ile Glu Ala Thr Arg Asn Leu Ala Thr Thr
 1               5                  10                  15 gag cga tgc atc caa gat att cga aat gcg cca gtg cga aat cgt tcc        96
Glu Arg Cys Ile Gln Asp Ile Arg Asn Ala Pro Val Arg Asn Arg Ser
            20                  25                  30 acg cag ttc cag ctg gct cag caa aac atg ctc gcc tac acc ttc ggt       144
Thr Gln Phe Gln Leu Ala Gln Gln Asn Met Leu Ala Tyr Thr Phe Gly
        35                  40                  45 gag gta atc cct gga ttc gct tca gct ggg att aac gga atg aac tat       192
Glu Val Ile Pro Gly Phe Ala Ser Ala Gly Ile Asn Gly Met Asn Tyr
    50                  55                  60 cgg gac gta att ggg cgc ccc gtt gaa aat gcc gtg aca gag gga act       240
Arg Asp Val Ile Gly Arg Pro Val Glu Asn Ala Val Thr Glu Gly Thr
65                  70                  75                  80 cac ttt ttc cga gac gat ttt cgc gta gat tca aat gca aag gcg aag       288
His Phe Phe Arg Asp Asp Phe Arg Val Asp Ser Asn Ala Lys Ala Lys
                85                  90                  95 gtt gcc ggc gat att ttc gag att gtg tct tct gcg gtc atg tgg aac       336
Val Ala Gly Asp Ile Phe Glu Ile Val Ser Ser Ala Val Met Trp Asn
            100                 105                 110 tgc gcg gct cgg tgg aac tcg ctg atg gtg ggt gaa ggg tgg cgc tct       384
Cys Ala Ala Arg Trp Asn Ser Leu Met Val Gly Glu Gly Trp Arg Ser
        115                 120                 125 cag ccg cgg tac agt agg ccg acg ctg agt ccg tct cct cgc cga caa       432
Gln Pro Arg Tyr Ser Arg Pro Thr Leu Ser Pro Ser Pro Arg Arg Gln
    130                 135                 140 gtg gca gtt ttg aat ttg ccg cgc agc ttt gac tgg gtc agc ctt ctg       480
Val Ala Val Leu Asn Leu Pro Arg Ser Phe Asp Trp Val Ser Leu Leu
145                 150                 155                 160 gtc ccc gaa tcg cag gaa gtg att gag gaa ttc agg gca ggc ctt cgg       528
Val Pro Glu Ser Gln Glu Val Ile Glu Glu Phe Arg Ala Gly Leu Arg
                165                 170                 175 aaa gat ggc ctc ggg ctc ccc act tct act ccc gat ttg gca gta gtt       576
Lys Asp Gly Leu Gly Leu Pro Thr Ser Thr Pro Asp Leu Ala Val Val
            180                 185                 190
```

```
gtc ctc ccg gaa gag ttc cag aat gat gaa atg tgg cgg gaa gaa ata      624
Val Leu Pro Glu Glu Phe Gln Asn Asp Glu Met Trp Arg Glu Glu Ile
            195                 200                 205 gca ggg ctg acg cgc cct aat caa att ctt ctt tcg gga gca tat cag      672
Ala Gly Leu Thr Arg Pro Asn Gln Ile Leu Leu Ser Gly Ala Tyr Gln
        210                 215                 220 cgg ctc caa ggg cgg gtt cag cct gga gag att tcc ctg gct gtg gcc      720
Arg Leu Gln Gly Arg Val Gln Pro Gly Glu Ile Ser Leu Ala Val Ala
225                 230                 235                 240 ttt aag agg agc ctt cga agt gat cgg ctg tat cag ccg ctc tac gag      768
Phe Lys Arg Ser Leu Arg Ser Asp Arg Leu Tyr Gln Pro Leu Tyr Glu
                245                 250                 255 gcg aac gtt atg cag ttg ctg ctt gag ggt aag ctt ggt gcg ccc aag      816
Ala Asn Val Met Gln Leu Leu Leu Glu Gly Lys Leu Gly Ala Pro Lys
            260                 265                 270 gtg gaa ttc gag gtt cat acg ctt gct cct gag ggc aca aat gcc ttc      864
Val Glu Phe Glu Val His Thr Leu Ala Pro Glu Gly Thr Asn Ala Phe
        275                 280                 285 gtt acg tat gaa gcg gca tca ctg tat ggg ttg gcg gaa ggg agg tca      912
Val Thr Tyr Glu Ala Ala Ser Leu Tyr Gly Leu Ala Glu Gly Arg Ser
    290                 295                 300 gcc gta cat cga gca atc cgg gag ctc tat gtt ccg ccg acc gct gcc      960
Ala Val His Arg Ala Ile Arg Glu Leu Tyr Val Pro Pro Thr Ala Ala
305                 310                 315                 320 gat ctc gca cgc cgc ttc ttc gcg ttc ttg aac gaa cgc atg gag ctg     1008
Asp Leu Ala Arg Arg Phe Phe Ala Phe Leu Asn Glu Arg Met Glu Leu
                325                 330                 335 gtg aac ggc tga                                                     1020
Val Asn Gly <210> SEQ ID NO 2
<211> LENGTH: 1290
<212> TYPE: DNA
<213> ORGANISM: Streptomyces griseus
<220> FEATURE:
<221> NAME/KEY: CDS
<222> LOCATION: (1)..(1287)

<400> SEQUENCE: 2 ttg acc cgc tgt cag tcc tcc cgg ata gcc tgt tgg ctt ccc acg aaa       48
Leu Thr Arg Cys Gln Ser Ser Arg Ile Ala Cys Trp Leu Pro Thr Lys
1               5                   10                  15 ggc tca cac tcc atg aca ccg cgc aag gcc gtc tct ctc ttc tca ggc       96
Gly Ser His Ser Met Thr Pro Arg Lys Ala Val Ser Leu Phe Ser Gly
            20                  25                  30 tgc gga ggc ttt tgc gag ggg gta cgc ctc gcc ggt ttt tca gtt gag      144
Cys Gly Gly Phe Cys Glu Gly Val Arg Leu Ala Gly Phe Ser Val Glu
        35                  40                  45 gca gcc gtc gag ctt gac cga ttc gct gca gtc acg tac cgc cac aac      192
Ala Ala Val Glu Leu Asp Arg Phe Ala Ala Val Thr Tyr Arg His Asn
    50                  55                  60 ttc ccc gaa gtt ccg ctt ttc gag gga gac gtt cat gac ttc ctc aat      240
Phe Pro Glu Val Pro Leu Phe Glu Gly Asp Val His Asp Phe Leu Asn
65                  70                  75                  80 gac tcg tcg gag acg tgg cgt ggc gaa gca gag aga ttc tcc gac gta      288
Asp Ser Ser Glu Thr Trp Arg Gly Glu Ala Glu Arg Phe Ser Asp Val
                85                  90                  95 aaa gca ggg aat att gac ctg ctc ttc gga ggg ccc cca tgc cag ggc      336
Lys Ala Gly Asn Ile Asp Leu Leu Phe Gly Gly Pro Pro Cys Gln Gly
            100                 105                 110
```

-continued

```
tac agt cag att ggc acc aga atc ctg gac gat ccc cgt aat caa ctg      384
Tyr Ser Gln Ile Gly Thr Arg Ile Leu Asp Asp Pro Arg Asn Gln Leu
        115                 120                 125 tac gcg gaa tat gtg cgg gtt ctt aag act ctc cgc cct cgc gtt ttc      432
Tyr Ala Glu Tyr Val Arg Val Leu Lys Thr Leu Arg Pro Arg Val Phe
    130                 135                 140 ttg atg gag aat gtc cca aac atg ctc cta atg gac aag ggt cgg ttc      480
Leu Met Glu Asn Val Pro Asn Met Leu Leu Met Asp Lys Gly Arg Phe
145                 150                 155                 160 aag cgc gag gtg ttg gca gct ttc gca gag gcc ggc tat tcg aat tgc      528
Lys Arg Glu Val Leu Ala Ala Phe Ala Glu Ala Gly Tyr Ser Asn Cys
                165                 170                 175 ggc gtg aca gtt gtt gca gcc tcg gat cac gga gtt ccc caa ctc cgg      576
Gly Val Thr Val Val Ala Ala Ser Asp His Gly Val Pro Gln Leu Arg
            180                 185                 190 cgc aga gcc att ttc ttc ggc gtt cgc gat ggg gaa aac cta ggc gtt      624
Arg Arg Ala Ile Phe Phe Gly Val Arg Asp Gly Glu Asn Leu Gly Val
        195                 200                 205 gac gca cat gct ttt cta gaa gct gct ctc gcg gcc gaa cgg aag cct      672
Asp Ala His Ala Phe Leu Glu Ala Ala Leu Ala Ala Glu Arg Lys Pro
    210                 215                 220 gaa gtt tct gta cgt cag gct atc ggc gat ctc ccg gaa gtg act gct      720
Glu Val Ser Val Arg Gln Ala Ile Gly Asp Leu Pro Glu Val Thr Ala
225                 230                 235                 240 agt cac tac gag ccg gtg cgc tac cct gtc acc cgc gca aaa aat ccg      768
Ser His Tyr Glu Pro Val Arg Tyr Pro Val Thr Arg Ala Lys Asn Pro
                245                 250                 255 ttc ctc gac gag atg cga ctg aac cgc gat ggc cag tgg tat tca cgc      816
Phe Leu Asp Glu Met Arg Leu Asn Arg Asp Gly Gln Trp Tyr Ser Arg
            260                 265                 270 gca gag aag tcc aaa aaa tcc act gcc aag gtt ctc cac aac cat cac      864
Ala Glu Lys Ser Lys Lys Ser Thr Ala Lys Val Leu His Asn His His
        275                 280                 285 acc aaa gag att caa gcc cgc cgg aaa gcc ctt atc gca ctc ctg gct      912
Thr Lys Glu Ile Gln Ala Arg Arg Lys Ala Leu Ile Ala Leu Leu Ala
    290                 295                 300 cca ggc gct aaa gca gat tcc cta ccg aaa gaa atc tgg aat ggt gcg      960
Pro Gly Ala Lys Ala Asp Ser Leu Pro Lys Glu Ile Trp Asn Gly Ala
305                 310                 315                 320 cgc ctt gag aag tgg cga cga ctg cac cca gac aag ccg gca tac acg     1008
Arg Leu Glu Lys Trp Arg Arg Leu His Pro Asp Lys Pro Ala Tyr Thr
                325                 330                 335 att ttg gcg cag atg cat cgc gac atg tct gaa tgg gtg cat cct gac     1056
Ile Leu Ala Gln Met His Arg Asp Met Ser Glu Trp Val His Pro Asp
            340                 345                 350 tat gag cga tgg atc act gtt cgc gag gca gcg cgc ctc cag tct ttc     1104
Tyr Glu Arg Trp Ile Thr Val Arg Glu Ala Ala Arg Leu Gln Ser Phe
        355                 360                 365 cat gat gga ttc gta ttc cag acc agc gaa tgg cag atg ttg aag cag     1152
His Asp Gly Phe Val Phe Gln Thr Ser Glu Trp Gln Met Leu Lys Gln
    370                 375                 380 atc gga aac gcc gtt cct ccg ctg atg gca cgg gct ttg gca gct gtt     1200
Ile Gly Asn Ala Val Pro Pro Leu Met Ala Arg Ala Leu Ala Ala Val
385                 390                 395                 400 gcg agc cgt tca ctg gac gtg atg gaa gat tca tct acg gac acg cgg     1248
Ala Ser Arg Ser Leu Asp Val Met Glu Asp Ser Ser Thr Asp Thr Arg
                405                 410                 415
```

```
ttt agc gtc ccg att cag cag acg ttg gaa cta gtg ccc tga        1290
Phe Ser Val Pro Ile Gln Gln Thr Leu Glu Leu Val Pro
        420                 425
```

<210> SEQ ID NO 3
<211> LENGTH: 240
<212> TYPE: DNA
<213> ORGANISM: Streptomyces griseus
<220> FEATURE:
<221> NAME/KEY: CDS
<222> LOCATION: (1)..(237)

<400> SEQUENCE: 3

```
gtg cct gac ctg tgc tct cac ctt ggc ttg gct gta cgt gct gtg agg    48
Val Pro Asp Leu Cys Ser His Leu Gly Leu Ala Val Arg Ala Val Arg
 1               5                  10                  15 ctg cga cgc ggc tgg tct cag gag ctg ttg tcg gaa aaa tct gga ttg    96
Leu Arg Arg Gly Trp Ser Gln Glu Leu Leu Ser Glu Lys Ser Gly Leu
            20                  25                  30 gat cgc aca tat gtg agt ggc ctt gag cgc ggg cgg cgg aac cct gcg   144
Asp Arg Thr Tyr Val Ser Gly Leu Glu Arg Gly Arg Arg Asn Pro Ala
        35                  40                  45 cta ctc acc ttg gcc cgt ttg gct gat gcg ctt gaa gtt ccg ttg tct   192
Leu Leu Thr Leu Ala Arg Leu Ala Asp Ala Leu Glu Val Pro Leu Ser
    50                  55                  60 gag cta atc cgt gat gcc gag gag aat tca ggt gcc ctt tac tta tag   240
Glu Leu Ile Arg Asp Ala Glu Glu Asn Ser Gly Ala Leu Tyr Leu
65                  70                  75
```

<210> SEQ ID NO 4
<211> LENGTH: 29
<212> TYPE: PRT
<213> ORGANISM: Streptomyces griseus
<220> FEATURE:
<223> OTHER INFORMATION: "Xaa" in position 10, 18, 19 and 25 are
               unknown.

<400> SEQUENCE: 4

```
Met Phe Thr Tyr Ser Ile Glu Ala Thr Xaa Asn Leu Ala Thr Thr Glu
 1               5                  10                  15

His Xaa Xaa Ile Gln Asp Ile Arg Xaa Asn Ala Pro Val
            20                  25
```

<210> SEQ ID NO 5
<211> LENGTH: 16
<212> TYPE: PRT
<213> ORGANISM: Streptomyces griseus
<220> FEATURE:
<223> OTHER INFORMATION: At positions 7, 9, 14 and 16, "Xaa" is unknown

<400> SEQUENCE: 5

```
Met Val Gly Glu Gly Trp Xaa His Xaa Ser Gln Pro Gly Xaa Tyr Xaa
 1               5                  10                  15
```

<210> SEQ ID NO 6
<211> LENGTH: 6
<212> TYPE: PRT
<213> ORGANISM: Streptomyces griseus

<400> SEQUENCE: 6

```
Phe Thr Tyr Ser Ile Glu
 1               5
```

<210> SEQ ID NO 7
<211> LENGTH: 6

```
<212> TYPE: PRT
<213> ORGANISM: Bacillus stearothermophilus

<400> SEQUENCE: 7

Met Val Gly Glu Gly Trp
 1               5

<210> SEQ ID NO 8
<211> LENGTH: 17
<212> TYPE: DNA
<213> ORGANISM: Bacillus stearothermophilus
<220> FEATURE:
<223> OTHER INFORMATION: "n" in position 6 is any nucleic acid

<400> SEQUENCE: 8
ttyacntaya gyathga                                                    17

<210> SEQ ID NO 9
<211> LENGTH: 18
<212> TYPE: DNA
<213> ORGANISM: Streptomyces griseus
<220> FEATURE:
<223> OTHER INFORMATION: "n" at position 4, 10 and 13 are any nucleic
                        acid

<400> SEQUENCE: 9
ccanccytcn ccnaccat                                                   18

<210> SEQ ID NO 10
<211> LENGTH: 20
<212> TYPE: DNA
<213> ORGANISM: Streptomyces griseus

<400> SEQUENCE: 10
gactatcggg acgtaattgg                                                 20

<210> SEQ ID NO 11
<211> LENGTH: 20
<212> TYPE: DNA
<213> ORGANISM: Streptomyces griseus

<400> SEQUENCE: 11
cattccgtta atcccagctg                                                 20

<210> SEQ ID NO 12
<211> LENGTH: 17
<212> TYPE: DNA
<213> ORGANISM: Streptomyces griseus

<400> SEQUENCE: 12
tcgggctccc cacttct                                                    17

<210> SEQ ID NO 13
<211> LENGTH: 21
<212> TYPE: DNA
<213> ORGANISM: Streptomyces griseus

<400> SEQUENCE: 13
ggccatcttt ccgaaggcct g                                               21

<210> SEQ ID NO 14
<211> LENGTH: 22
<212> TYPE: DNA
<213> ORGANISM: Streptomyces griseus
```

```
<400> SEQUENCE: 14
caatctttct ggatcctact tg                                          22

<210> SEQ ID NO 15
<211> LENGTH: 44
<212> TYPE: DNA
<213> ORGANISM: Streptomyces griseus

<400> SEQUENCE: 15
cgcggatcct aaggaggtga tcaggtgccc tttacttata gcat                  44

<210> SEQ ID NO 16
<211> LENGTH: 30
<212> TYPE: DNA
<213> ORGANISM: Streptomyces griseus

<400> SEQUENCE: 16
aaccctcgag cctttcagcc gttcaccagc                                  30
```